United States Patent [19]

Shen et al.

[11] Patent Number: 5,144,011

[45] Date of Patent: * Sep. 1, 1992

[54] ACIDITY-SENSITIVE SPACER MOLECULE TO CONTROL THE RELEASE OF PHARMACEUTICALS FROM MOLECULAR CARRIERS

[75] Inventors: Wei C. Shen, Needham; Hugues J.-P. Ryser, Concord, both of Mass.

[73] Assignee: Boston University, Boston, Mass.

[ * ] Notice: The portion of the term of this patent subsequent to Dec. 23, 2003 has been disclaimed.

[21] Appl. No.: 308,960

[22] Filed: Feb. 6, 1989

Related U.S. Application Data

[63] Continuation of Ser. No. 924,821, Oct. 30, 1986, abandoned, which is a continuation of Ser. No. 277,633, Jun. 26, 1981, Pat. No. 4,631,190.

[51] Int. Cl.$^5$ .................... C07K 17/06; A61K 39/44; A61K 47/48

[52] U.S. Cl. .................... 530/391.5; 530/345; 530/391.9; 530/404; 530/405; 530/406; 530/408; 530/409; 530/410; 424/85.8; 424/85.91; 435/7.1; 435/174; 435/188; 525/51.1; 549/60; 549/62; 562/512; 210/635

[58] Field of Search ................ 424/85.8, 35.91; 435/7, 435/174, 188; 530/345, 389, 390, 391, 404, 405, 406, 408, 409, 410, 391.5, 391.9; 525/54.1; 549/60, 62; 562/512; 210/635

[56] References Cited

U.S. PATENT DOCUMENTS

| | | | |
|---|---|---|---|
| 3,905,871 | 9/1975 | Ruberstein et al. | 435/7 |
| 3,978,203 | 8/1976 | Wise | 424/85 |
| 4,046,722 | 9/1977 | Rowland | 424/85 |
| 4,093,607 | 6/1978 | Sela et al. | 530/391.9 |
| 4,137,401 | 1/1979 | Lemieux et al. | 536/116 |
| 4,181,786 | 1/1980 | Mune et al. | 525/327 |
| 4,202,323 | 5/1980 | Zweig et al. | 128/1.1 |
| 4,223,013 | 9/1980 | Hu et al. | 424/85 |
| 4,256,632 | 3/1981 | Levin et al. | 530/322 |
| 4,259,232 | 3/1981 | Carrico et al. | 530/391.1 |
| 4,259,233 | 3/1981 | Carrico et al. | 530/391.1 |
| 4,261,969 | 4/1981 | Heller | 424/19 |
| 4,261,974 | 4/1981 | Buckler et al. | 530/387.1 |
| 4,272,525 | 6/1981 | Wright | 424/177 |
| 4,275,000 | 6/1981 | Ross | 530/391 |
| 4,285,930 | 8/1981 | Likhite | 424/92 |
| 4,303,786 | 12/1981 | Goldstein et al. | 536/51 |
| 4,314,999 | 2/1982 | DeBarbieri | 514/8 |
| 4,542,225 | 9/1985 | Blatter et al. | 548/473 |
| 4,631,190 | 12/1986 | Shen et al. | 424/85.8 |

OTHER PUBLICATIONS

Dixon et al (1968) Biochem. J. 109:312-314.
Gibbons et al (1970) Biochem J. 116:843-849.
Heller et al., "Controlled Drug Release by Polymer Dissolution . . . ", *J. Applied Polymer Science*, 22: 1991-2009 (1978).
Masquelier et al., "Amino Acid and Dipeptide Derivatives of Daunoymcin . . . ", *J. Med. Chem.*, 23:1166-1170 (1980).
Yatvin et al., "pH-Sensitive Liposome: Possible Clinical Implications," *Science*, 210: 1253-1255 (12 Dec. 1980).
Shen et al., "Cis-Aconityl Spacer Between Daunomycin . . . ," *Biochem. Biophys. Res. Commun.*, 102(3): 1048-1054 (Oct. 15, 1981).
Trouet, "Increased Selectivity of Drugs by Linking to Carriers," *Europ. J. Cancer*, 14:105-111 (1978).
Ryser et al., "Conjugation of Methotrexate to Poly (L-lysine) . . . ," *Proc. Natl. Acad. Sci. USA*, 75(8): 3867-3870 (Aug. 1978).

*Primary Examiner*—Christine M. Nucker
*Assistant Examiner*—Kay K. Kim
*Attorney, Agent, or Firm*—Hamilton, Brook, Smith & Reynolds

[57] ABSTRACT

A method for controlling the release of durgs or other passenger molecules form carrier conjugates, and a class of conjugates that releases drugs when ingested by a cell or subjected to acidic conditions, are disclosed. These conjugates contain a passenger molecule which is attached to a spacer molecule through an acidic bonding group, such as carboxyl, that is in a "cis" configuration with another acidic group, and a carrier molecule that is bonded to the spacer molecule at another site. When subjected to a mild increase in acidity, such as occurs within a lysosome of a cell, the drug or other passenger molecule is hydrolyzed from the the conjugate and released in unmodified, active form.

12 Claims, 1 Drawing Sheet

RELEASE OF DM FROM CIS-ACONITIC SPACER MOLECULE

RELEASE OF DM FROM CIS-ACONITIC
SPACER MOLECULE

ACIDITY-SENSITIVE SPACER MOLECULE TO CONTROL THE RELEASE OF PHARMACEUTICALS FROM MOLECULAR CARRIERS

GOVERNMENT SUPPORT

Work relating to this invention was partially supported by grants from the National Cancer Institute and the National Institutes of Health.

This is a continuation of co-pending application Ser. No. 06/924,821 filed on Oct. 30, 1986, now abandoned which is a continuation of Ser. No. 06/277,633 filed Jun. 26, 1981, now U.S. Pat. No. 4,631,190, the contents of both applications are hereby incorporated by reference.

TECHNICAL FIELD

This invention is in the fields of chemistry, cell biology, medicine, and pharmacology.

BACKGROUND ART

Molecular conjugates are formed by covalently bonding two or more molecules to each other. Such conjugates may exhibit useful properties that combine, exceed or differ from the properties of the components. For example, our U.S. patent application Ser. No. 002,368 now U.S. Pat. No. 4,701,521 ("Method of Effecting Cellular Uptake of Molecules," filed on Jan. 10, 1979) describes a method of bonding anti-cancer drugs which enter cells at low rates to cationic polymers which enter cells at relatively higher rates. Such drugs enter cells at higher rates when administered in conjugate form than when administered as unmodified drug.

Certain molecular conjugates, such as the conjugate mentioned above, may be referred to as macromolecular drug carriers. The components of such conjugates may be regarded as *carriers* or *passengers*, depending upon their primary function. The primary purpose of a carrier in the context of this invention is to increase the transport and delivery of a passenger molecule to a desired location. Once the carrier reaches a desired location, it may perform other functions. Passenger molecules may comprise drugs, antibodies, antigens, lectins, dyes, stains, tracers, or other substances that perform at least one useful function upon reaching a desired location with the aid of a carrier molecule.

According to current concepts of cell biology, ingested macromolecular carriers are transported to lysosomes where they are subjected to the action of lysosomal enzymes [1]. If a carrier is a proper substrate for one or more of these enzymes, it normally is hydrolyzed and is digested into diffusible metabolites. Such metabolites are normally excreted or reutilized.

In addition to containing hydrolytic enzymes, lysosomes tend to be substantially more acidic than other compartments or fluids within a cell or body. For example, the pH of blood is about 7.3 to 7.4 [2]. However, the pH of a lysosome is about 4.8 [3], and it has been suggested that the pH within a lysosome can be as low as 3.8 during the initial stage of digestion [4].

Conjugation of a drug to a carrier molecule may reduce the desired activity of the drug until the carrier is hydrolyzed or digested. There are at least two mechanisms by which this may occur. First, conjugation may alter the size or shape of a drug, thereby impeding steric interaction with a target molecule. For example, the anti-cancer drug methotrexate kills cells by binding to and inactivating an essential enzyme, dihydrofolate reductase (DHFR). Conjugation of methotrexate to poly(lysine) causes steric hindrance which substantially reduces the ability of methotrexate to inactivate DHFR. However, when the poly(lysine) is digested or hydrolyzed, the methotrexate recovers its activity. Second, conjugation may alter a functional group that is essential for pharmacological activity. For example, in certain drugs like Daunomycin, the chemical group that normally is most suitable for conjugation is a functional amine group. When Daunomycin is linked to another molecule through that group, the resulting conjugate is much less pharmacologically active. The Daunomycin recovers its full activity only if it is released from the conjugate in unmodified form.

A drug-carrier conjugate that relies upon enzymatic processes to break the conjugate into its components, thereby reactivating the drug, is subject to certain limitations, including the following. First, certain carriers and conjugates may not be susceptible to lysosomal hydrolysis. Second, enzymatic action may release a modified, less active form of the passenger drug. Third, certain carriers and drugs may inhibit or modify the normal enzymatic functions of lysosomes.

For these and other reasons, it would be useful to achieve the cleavage of drug-carrier linkages by non-enzymatic techniques. This can be achieved by taking advantage of the acidic pH of lysosomes by creating molecular conjugates that are sensitive to mild acidity, such as exists in the interior of a lysosome.

DISCLOSURE OF THE INVENTION

This invention relates to molecular conjugates which are subject to spontaneous hydrolysis under mild acidic conditions. Such conjugates contain three types of component molecules, which can be designated as "carrier," "spacer," and "passenger" molecules. The spacer molecule must contain at least two active sites that are amenable to the formation of covalent bonds with the other two component molecules. At least one site comprises an acidic group that is in a "cis" configuration with another acidic group. At least one other site capable of conjugating with a carrier molecule is located elsewhere on the spacer molecule.

A conjugate of this invention is formed by a sequence of at least two conjugation steps. During at least one first conjugation step, the relatively more reactive cis-acidic site on the spacer molecule forms a covalent bond with a drug or other passenger molecule, to form a drug-spacer conjugate. During at least one second conjugation step, the drug-spacer conjugate reacts through the less reactive site of the spacer molecule with a carrier molecule. The result is a conjugate containing carrier and passenger molecules that are covalently bonded to a spacer molecule, but not to each other. Within the claims, carrier molecules are referred to as "first molecules"; spacer molecules are referred to as "second molecules"; and passenger molecules are referred to as "third molecules".

The carrier-spacer-passenger conjugate normally is formed and must be stored in a relatively neutral or alkaline environment. When the conjugate is subjected to an increase in acidity, the spacer-passenger bond decreases in strength due to a neighboring group effect involving the other acidic group in the cis configuration. This allows the passenger molecule to be preferentially released from the conjugate when the conjugate reaches a lysosome or other acidic environment. The passenger molecule may be a drug, a dye or stain, a radioactive tracer, or some other type of substance that performs at least one useful function after being released from the conjugate.

This invention provides a method of releasing passenger molecules from conjugates in unmodified form. This is important in the use of drugs or other passenger molecules which are conjugated to carrier molecules through functional groups that are required for pharmacologically activity, or which suffer steric hindrance when conjugated to carrier molecules, or which are otherwise hindered or inactivated by conjugation to carrier molecules.

BEST MODE FOR CARRYING OUT THE INVENTION

Figure 1:
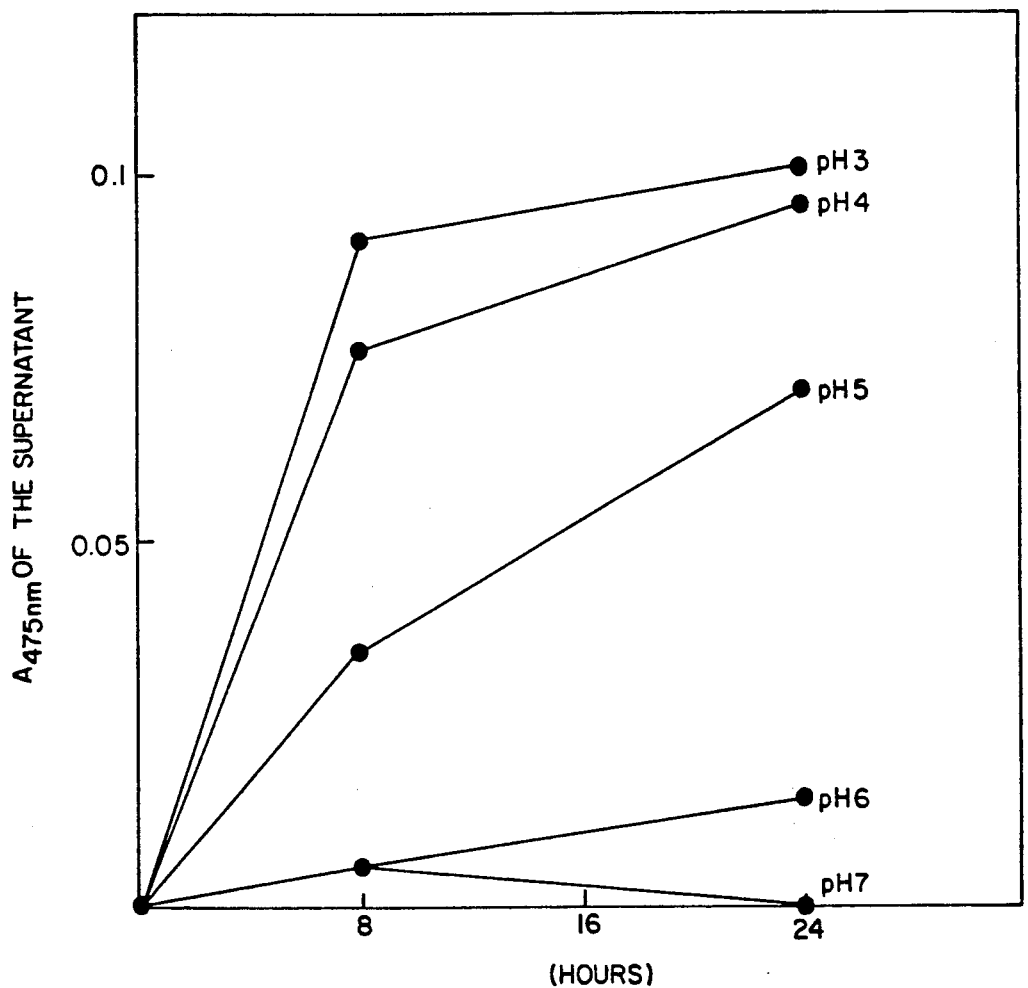
FIG. 1 is a graph indicating the relative amounts of Daunomycin released from ADM-Affi Gel 701 as a function of pH and time.

One preferred embodiment of a spacer molecule for use in this invention is a class of organic acids known as cis-polycarboxylic alkenes. This class of molecule contains at least three carboxylic acid groups (COOH) attached to a carbon chain that contains at least one double bond. At least one pair of carboxylic acid groups is in the "cis" configuration (i.e., they are bonded to adjacent unsaturated carbon atoms on the same side of the double bond), so that they are constrained in relatively close proximity to each other. At least one other carboxyl group is attached to the alkene molecule at a location other than a cis-carboxyl alkene structure.

One preferred embodiment of this type of spacer molecule comprises cis-aconitic acid. Its chemical configuration is diagrammed below. The carbon atoms that comprise the alkene backbone of the molecule are designated $\alpha$, $\beta$ and $\gamma$ for reference. The carboxyl group attached to the $\alpha$ carbon is referred to as the $\alpha$ carboxyl group, and so forth. The $\alpha$ and $\beta$ carboxyl groups are in the "cis" configuration.

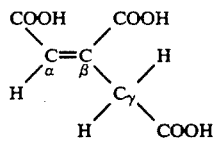

A passenger-spacer-carrier conjugate with the desired properties is created by bonding a passenger molecule to either of the $\alpha$ or $\beta$ carboxyl groups, while a carrier molecule is bonded to the $\gamma$ carboxyl group. This configuration is shown below, where PM represents a passenger molecule and CM represents a carrier molecule. It is believed that $\alpha$ and $\beta$ isomers normally are comparable for the purposes of this invention; this may be determined by routine experimentation using conjugates involving specific passenger and carrier molecules.

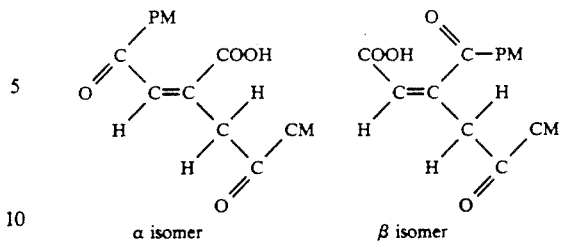

This reaction is normally accomplished using aconityl anhydride, which has the following structural formula:

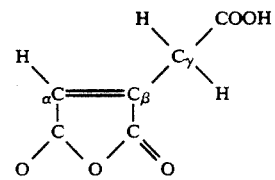

The ring structure which contains $\alpha$ and $\beta$ carbon atoms is referred to herein as a maleic anhydride ring. It is relatively reactive, and when a substance that contains a maleic anhydride ring is dissolved in water, the ring is usually hydrolyzed into cis-carboxyl groups. If a substance that contains a maleic anhydride ring reacts with a passenger molecule that contains a nucleophilic group, the normal result is for one of the cis-carboxyl groups to be converted into carboxylic acid while the other cis-carboxyl group becomes attached to the nucleophilic group of the passenger molecule. This reaction is shown, using aconityl anhydride as an example, by the following formula:

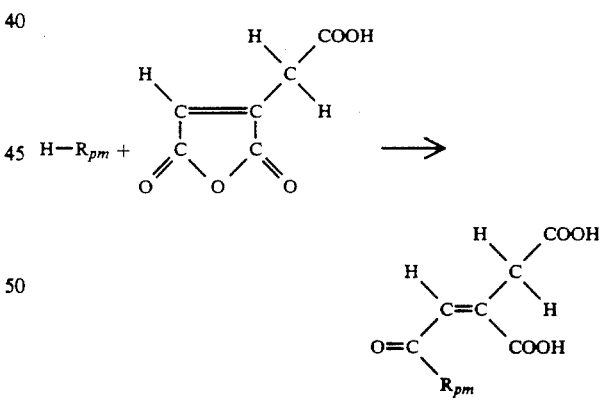

where H—$R_{pm}$ is a passenger molecule.

When one carboxyl group in a cis-carboxyl pair is conjugated with a nucleophilic group of another molecule, the other cis-carboxylic acid group is less reactive, than the $\gamma$-carboxyl group. Therefore, a substance added during the second stage of a conjugation process will tend to react with the $\gamma$-carboxyl group, rather than with the remaining cis-carboxylic acid group. This allows a carrier molecule to be attached to a $\gamma$-carboxyl group after a passenger molecule has been attached to one of the cis-carboxyl groups, as shown in the following example:

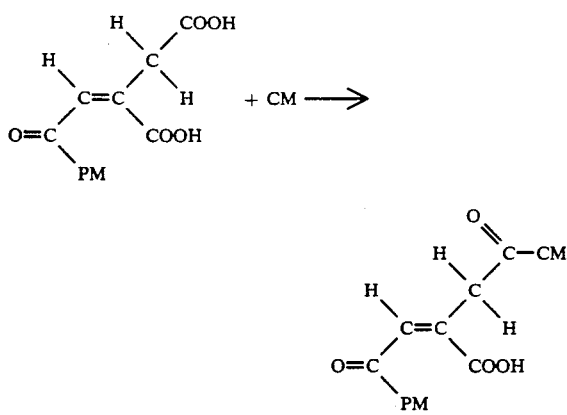

where PM represents a passenger molecule and CM represents a carrier molecule. This series of reactions provides relatively high yields of carrier-spacer-passenger conjugates with desired configurations.

In one preferred embodiment of this invention, a single passenger molecule comprising the drug Daunomycin is covalently bonded to a cis-carboxyl group (an α or β carboxyl) on a spacer molecule comprising cis-aconitic acid. This passenger-spacer conjugate is then covalently bonded through the γ-carboxyl group of the spacer molecule to a carrier molecule comprising polylysine. The entire conjugate is administered to a cell culture or an animal or human. The conjugate is readily taken into cells, and transported to lysosomes, where it is subjected to more acidic conditions than exist in the bloodstream or extracellular medium. Under such conditions, the cis-carboxyl bond is weakened, and the Daunomycin is released from the spacer molecule in unaltered form. This allows the drug to accomplish its intended purpose. Through endogenous processes, the cell eventually metabolizes the carrier and utilizes the resulting lysine and the cis-aconitic spacer.

OTHER MODES OF CARRYING OUT THIS INVENTION

In a preferred embodiment of this invention, it is possible to transpose the passenger and carrier molecules by altering the sequence of reactions. This would cause the carrier molecule to be cleaved more readily from the conjugate under acidic conditions.

An alternate preferred embodiment of this invention involves spacer molecules with multiple cis-carboxyl groups. Such compounds can be formed by hydrolyzing any of several substances which contain more than one maleic anhydride ring. One such polyanhydride which is commercially available in crystalline form comprises copoly(ethyl maleic anhydride), commonly referred to as PEMA, which has the following repetitive unit, where n is a large integer:

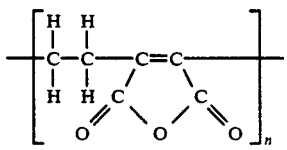

Other poly-maleic anhydrides are also commercially available.

Each pair of cis-carboxyl groups formed by hydrolyzing a maleic anhydride is believed to comprise a suitable location for bonding a passenger molecule or a carrier molecule. Therefore, numerous passenger molecules may be bonded to a single polymeric spacer molecule. This allows for the transport of numerous passenger molecules to a desired acidic region, and for the release of large numbers of passenger molecules by the conjugate in that region, thereby increasing the efficiency of the conjugate.

The use of polymeric spacer molecules allows for the transport of different types of drugs or other passenger molecules conjugated to a single carrier, and the spontaneous release of such passenger molecules from the spacer when the conjugate is subjected to acidic conditions. Such formulations may be useful in the treatment of cancer, tuberculosis and other diseases that often require a combination of drugs. For example, both Daunomycin and Bleomycin may be bonded to carboxyl groups. Therefore, both of these drugs may be bonded to a single polymeric spacer molecule, and released in unaltered form in an acidic environment.

Any type or source of poly-cis-carboxylic molecules might be suitable for use with this invention, as can be determined through routine experimentation by someone skilled in the art. In addition, there is no minimum number of maleic anhydride rings or cis-carboxylic groups upon which this invention depends. Cis-carboxylic alkadienes and alkatrienes, as well as cis-aconitic acid and polymeric anhydrides, are suitable for use as spacer molecules according to this invention.

This invention relates to the use, as a spacer molecule, of a molecule that has two or more bonding groups that create bonds that are dissimilar in strength when subjected to acidity. Such bonding groups are not limited to carboxyl groups. For example, the γ-carboxyl group of cis-aconitic acid may be replaced by any functional group R that is capable of forming a covalent bond with a carrier molecule.

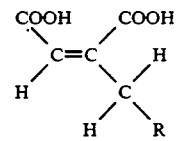

In addition, acidic groups other than carboxylic acid may be useful in spacer molecules. For example, sulfide groups are acidic, and a sulfide group in a cis-configuration with a carboxyl group may have pH-sensitivity comparable to cis-dicarboxylic groups.

Spacer molecules that are sensitive to acidity can be utilized at more than one location within certain carrier-passenger complexes. For example, U.S. Pat. No. 4,046,722 involves a three-part complex. An immunoglobulin serves as the carrier. From one to ten polymers (such as activated dextran) are attached to each immunoglobulin. From five to 500 molecules of a cytotoxic drug are covalently bonded to each polymer. Acid-sensitive spacer molecules could be inserted into such a complex at two categories of locations. If inserted between the immunoglobulin and a polymer, then the polymer with its numerous cytotoxic drug molecules would be released from the immunoglobulin when the entire complex is subjected to increasing acidity. If acid-sensitive spacer molecules are inserted between a polymer and a cytotoxic drug, the cytotoxic drug would be released from the immunoglobulin-polymer complex when subject to increasing acidity.

Antibodies, lectins, and other substances which may become attached to the surface of a cell may be useful as carriers for the purpose of this invention, in either of two ways. First, a conjugate that becomes attached to the surface of a cell normally is eventually ingested into the cell by means of a process such as endocytosis or pinocytosis. Once ingested, the conjugate is transported to the lysosome, and is hydrolyzed or digested as described above, which cleaves the passenger-spacer bond and releases the passenger molecule in unmodified, active form. Second, many types of cancer cells excrete lactic acid, which causes the microenvironment of many tumor cells to be acidic. Therefore, conjugates that attach to cancerous cells in a tumor will be gradually and spontaneously hydrolyzed, releasing anti-cancer drugs in unmodified, active form. The rate of hydrolysis is dependent upon the level of acidity of the microenvironment. Since the microenvironment of tumors is usually not highly acidic, the release of drug molecules from conjugates may occur slowly and over an extended period of time. This may be desirable in the treatment of a tumor.

Passenger molecules should be broadly construed. In general, a passenger molecule may comprise any molecule that performs at least one useful function after it reaches a certain region of a body, a cell, or a vessel. Passenger molecules may comprise any type of substance that performs a useful function, including drugs (broadly defined as "any chemical agent that affects any living process" [5]), antibodies, antigens, lectins, dyes, stains, and tracers.

EXAMPLES

This invention is further explained and illustrated by the following examples.

EXAMPLE 1

Preparation of Aconityl-Daunomycin (ADM) Conjugate 5 mg of Daunomycin (DM) was dissolved in 1 ml of 0.1 $Na_2HPO_4$ in a test tube. This solution was cooled in an ice bath and slowly stirred while 5 mg of aconityl anhydride was added. The pH was kept at 9 by careful addition of 1N NaOH. The reaction mixture was stirred for 10 minutes in an ice bath and then for 10 minutes at room temperature The mixture was diluted to 3 ml with cold water and cooled again in an ice bath. 1N HCl was added slowly while the solution was stirred in an ice bath until formation of a heavy precipitate. After sitting in ice for ½ hour, the precipitate was collected by centrifugation and redissolved in 4 ml water with added 1N NaOH. The solution was acidified again with 1N HCl and the final precipitate was dissolved in 0.5 ml water with the addition of 1N NaOH to adjust the final pH to about 8. The concentration of the product was determined by measuring light absorption at a wavelength of 475 nm ($\epsilon = 9860$). Approximately 80% of the Daunomycin was recovered as its cis-aconityl derivative. Thin-layer chromatography, using acetone: $CHCl_3$:acetic acid at the ratio of 17 3:1, indicated no detectable free Daunomycin in the final product (Rf: 0.20 for DM, 0.05 for ADM).

EXAMPLE 2

Conjugation of ADM to Affi Gel 701

A 1.7 ml aliquot of Affi Gel 701 (Bio-Rad, 3 umole/ml, 1-3 u) was centrifuged. The gel pellet was washed twice with 5 ml $H_2O$ and resuspended in 0 5 ml $H_2O$. ADM solution (0.13 ml of 7.5 mM) was added to the gel suspension and then 20 mg of 1-ethyl-3-(3-dimethylaminopropyl)-carbodiimide was added to the mixture while stirring. After 2 hours, reaction mixture was diluted to 5 ml with $H_2O$ and centrifuged. The amount of ADM conjugated to gel, which was estimated by the difference of unbound ADM in the supernatant before and after the 2 hour reaction, was 33% of the total ADM. Approximately 6.5% of the amino groups on the gel were modified. The conjugated gel precipitate was washed extensively with phosphate buffer saline (PBS), resuspended in PBS (pH 7) and kept at 4° C. No DM could be detected in the supernatant for the conjugate gel, even after 2 months storage at 4° C.

EXAMPLE 3 pH-Sensitive Release of DM from ADM-Affi Gel 701

Citrate-phosphate buffer (0.85 ml, 0.15M) of various pH's from 3 to 7 was added to test tubes containing 0.15 ml of ADM-Affi Gel 701 suspension. ([DM]=$1 \times 10^{-4}$ M). The mixtures were incubated at 37° C. for 8 and 24 hours. At each time, the incubated test tubes centrifuged and the absorption of the supernatant at 475 nm was measured. Results of the DM-release at pH 3, 4, 5, 6 and 7 are shown in FIG. 1.

The amount of releasable DM from ADM-Affi Gel 701, estimated by the maximal DM concentration in the supernatant of incubations at pH 3 and 4, was 67% of the total gel-bound ADM. The remaining 33% of gel-bound ADM could be ADM attached to gels by non-specific absorption or through linkages involving the $\alpha$ or $\beta$ carboxyl group of cis-aconitic acid.

Unaltered DM was released from ADM-Affi Gel 701 at low pH, as confirmed by thin-layer chromatography described as follows: A 50 ul of ADM-Affi Gel 701 suspension was diluted to 1 ml with $H_2O$. After centrifugation, the gel precipitate was resuspended in 20 ul of 0.1N acetic acid. The suspension was incubated at 37° C for 2 hours, and approximately 4 ul of the suspension was subjected to thin-layer chromatography. The product released from ADM-Affi Gel 701 was identified as DM. (Solvent, acetone:chloroform acetic acid - 17:3:1; Rf of DM=0.16, ADM=0.04, release product=0.16).

EXAMPLE 4

Conjugation of ADM to Poly-lysine

1-Ethyl-3-(3-dimethylaminopropyl)-carbodiimide (20 mg) was added to a mixture of ADM (1.2 mg) and poly(Lysine)(10 mg, 70,000 MW) in 0.4 ml $H_2O$. After a 17 hour reaction at 25° C, in darkness, the mixture was loaded in a Sephadex G-50 column (1.5×40 cm), and the column was eluted with phosphate buffered saline, pH 7. Each 1 ml fraction was collected and fractions at volumes with a dark red color (16–19 ml) were pooled. The concentration of DM in the pooled solution was estimated by the absorbance at 475 nm. The final conjugated product in the solution corresponded to 66% of the original ADM in the reaction mixture.

EXAMPLE 5

Growth-Inhibiting Effects of Daunomycin from ADM-Poly(Lysine) and MDM-Poly(Lysine)

WEHI-5 leukemia cells were seeded at $5 \times 10^4$ cells per 25 cm$^2$ flask and were grown for 24 hours before exposure to ADM-poly(Lys), prepared as described above. After 5 days exposure to ADM-poly(Lys), the number of cells in each flask was counted in a Coulter counter, and compared to the number of cells in flasks that were not subjected to the drug conjugates. In two separate experiments, the ADM-poly(Lys) conjugate killed 96.7 and 99.1% of the cells.

WEHI-5 cells, prepared as described in this example, were exposed to a conjugate comprising Daunomycin (DM) and poly(LYS) bonded to the carboxyl groups of maleic acid (MDM-poly(LYS)) as shown below:

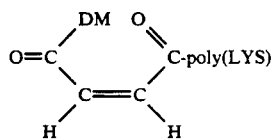

After 5 days exposure to MDM-poly(LYS), the number of cells in each flask was counted and compared to a control flask. In two experiments, the MDM-poly(LYS) conjugate killed only 6.7 and 4.3% of the cells.

Both of these results are displayed in Table 1. They indicate that a drug-carboxyl bond that is in a cis-configuration with a free acidic group is labile in the acidic conditions of a lysosome, while a drug-carboxyl bond that is not in a cis-configuration with a free acidic group is not labile in such conditions.

TABLE 1

| Drug Conjugate | Cytotoxicity of DM Conjugates | |
|---|---|---|
| ($1 \times 10^{-7}$M) | Cells Killed (%) | |
| | Exp. #1 | Exp. #2 |
| DM-aconitic-poly (LYS) | 99.1 | 96.7 |
| DM-maleic-poly (LYS) | 4.3 | 6.7 |

EXAMPLE 6 pH-Sensitive Release of Pharmacologically Active DM from ADM-Affi Gel 701

ADM-Affi Gel 701 gels, prepared as described above, were preincubated at 37° C in either pH 5 or pH 7 buffer. After 18 hours, small aliquots of the suspensions were added to the growth medium on top of WEHI-5 leukemia cells ($5 \times 10^4$ cells/25 cm$^2$). The final concentration of total DM (bound or free DM) in each flask was $1 \times 10^{-7}$ or $3 \times 10^{-7}$M. Appropriate aliquots of pH 5 or pH 7 buffer were added to control flasks and showed no effect on cell growth. After 3 days of growth in presence of the ADM-Affi Gel 701 aliquots, cells were allowed to grow for another 3 days in fresh medium without drug and then were counted in a Coulter Counter. The number of surviving cells in each flask expressed as percentage of the number of surviving cells in the control flasks, is shown in Table 2. This indicates that mild acidity releases DM from the Affi Gel-spacer-drug conjugate.

TABLE 2

| Cytotoxicity of ADM-Affi Gel 701 (percentage of cells killed) | | |
|---|---|---|
| Concentration of DM in ADM-Affi Gel 701 | pH 7 | pH 5 |
| $1 \times 10^{-7}$M | 4% | 27% |
| $3 \times 10^{-7}$M | 20% | 94% |

INDUSTRIAL APPLICABILITY

This invention has industrial applicability in any situation in which it is desired to release a passenger molecule from a carrier molecule when a passenger-carrier conjugate reaches an acidic location or is otherwise subjected to acidic conditions. Such uses may include industrial and non-medical processes. For example, one such use involves affinity chromatography. In this procedure, carriers would comprise solid matrix, such as beads packed into a column or other vessel. The passenger molecules would comprise specific ligands used to purify or analyze receptor molecules. Normally, a ligand is bound directly to a bead or other solid matrix. The bound receptor molecules normally are eluted from the vessel by means of high salt or excess free ligand solution. Such procedures may require further purification to remove salt or free ligand from the eluent. However, the use of a pH-sensitive spacer molecule between a bead and a ligand would allow the ligand to be removed from the bead by the simple step of washing the carriers with a mild acidic solution. In addition to simplifying and enhancing the assay involved, this step is reversible and could allow for the regeneration of the beads by the subsequent addition of fresh ligands.

In any procedure where it is desirable to modify the physicochemical properties of a molecule by conjugating it to another molecule, it may be desirable to cleave the conjugate into its components at a subsequent time to recover the original molecule. Such recovery may be facilitated if the conjugate includes an acid-sensitive bond. Such conjugates may be formed by the methods of this invention. For example, it may be useful to reduce the hydrophobicity of a molecule to increase the ability of the molecule to pass through a filter, ion exchanger, membrane, or adsorption column. This may be accomplished by conjugating the molecule to a hydrophilic molecule. After the filtration, ion exchange, or adsorption process is complete, it may be desirable to cleave the conjugate into its component molecules to recover the hydrophobic molecule. If the conjugate contains an acidity-sensitive spacer molecule according to this invention, cleavage may be accomplished by the simple method of contacting the conjugate with an acid.

EQUIVALENTS

Those skilled in the art will recognize, or will be able to ascertain using no more than routine experimentation, numerous equivalents to the specific embodiments described herein. Such equivalents are within the scope of this invention.

REFERENCES

1. C. DeDuve et al, *Biochem. Pharmacol.* 23:2495-2431 (1974).
2. *Scientific Tables*, 6th edition, p. 551, Documenta Geigy (1962).
3. C. DeDuve et al, *Microenvironments and Metabolic Compartmentation*, p. 371-379, Academic Press, New York (1978) and S. Ohkuma et al, *Proc. Nat'l. Acad. Sci.* 75: 3327-331 (1978).

4. J. T. Dingle (ed.), *Lysosomes in Biology and Pathology,* Vol. 3., p. 89-137, North Holland Publ., Amsterdam (1973).

5. A. G. Gilman, et al, *The Pharmacological Basis of Therapeutics,* 6th edition, p. 1, Macmillan Publ., New York (1980).

We claim:

1. A molecular conjugate that is hydrolyzed when subjected to acidity, which comprises:
   a) a first molecule which is boned to a second molecule through a moiety that is not attached to said second molecule in a cis configuration with an acidic moiety;
   b) said second molecule comprising an alkene possessing at least two acidic moieties attached to said second molecule in a cis configuration; and
   c) a third molecule which is bonded to one of said acidic moieties attached to said second molecule in a cis configuration.

2. A molecular conjugate that is hydrolyzed when subjected to acidity, which comprises:
   a) a first molecule which is bonded to a second molecule through a moiety that is not attached to said second molecule in a cis configuration with an acidic moiety;
   b) said second molecule comprising an alkene with the following structural formula:

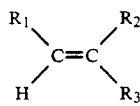

wherein $R_1$ and $R_2$ comprise any acidic groups and $R_3$ comprises any group that is capable of bonding to said first molecule; and
   c) a third molecule which is bonded to one of said acidic moieties attached to said second molecule in a cis configuration.

3. A molecular conjugate that is hydrolyzed when subjected to acidity, which comprises:
   a) a first molecule which is bonded to a second molecule through a moiety that is not attached to said second molecule in a cis configuration with an acidic moiety;
   b) said second molecule comprising an alkene with the following structural formula:

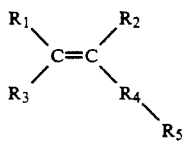

wherein $R_1$ and $R_2$ comprise any acidic groups, $R_3$ comprises an organic group or hydrogen, $R_4$ comprises $(CH_2)_n$ or $(CH)_n$ wherein n is an integer, and $R_5$ comprises any group that is capable of bonding to said first molecule; and
   c) a third molecule which is bonded to one of said acidic moieties attached to said second molecule in a cis configuration.

4. A molecular conjugate of claims 1, 2, or 3, wherein said second molecule is selected from the following group: cis-aconitic acid, cis-carboxylic alkadienes, cis-carboxylic alkatrienes, and hydrated poly-maleic anhydride rings.

5. A molecular conjugate of claims 1, 2, or 3, whereby more that one of said first molecule is bonded to at least one said second molecule.

6. A molecular conjugate of claims 1, 2, or 3, whereby more than one of said second molecule is bonded to at least one said first molecule.

7. A molecular conjugate of claims 1, 2, or 3, whereby more that one of said third molecule is bonded to at least one second molecule.

8. A molecular conjugate of claims 1, 2, or 3, whereby more than one type of second molecule is bonded to at least one third molecule.

9. A molecular conjugate of claims 1 and 2, wherein said acidic moieties that are attached to said second molecule in a cis-configuration are created by hydration of a maleic anhydride ring with the following structural formula:

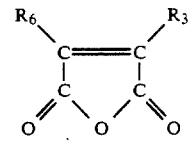

where $R_6$ comprises any organic group or hydrogen and $R_3$ comprises any organic group that is capable of bonding to said first molecule.

10. A molecular conjugate of claims 2 or 3, wherein $R_1$ and $R_2$ comprise a carboxyl group.

11. A molecular conjugate of claims 2 or 3, wherein $R_1$ and $R_2$ comprise a sulfide group.

12. A molecular conjugate of claim 3, wherein said acidic moieties that are attached to said second molecule in a cis-configuration are created by hydration of a maleic anhydride ring with the following structural formula:

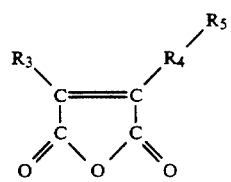

* * * * *